United States Patent [19]
Klebe

[11] Patent Number: 5,641,644
[45] Date of Patent: Jun. 24, 1997

[54] METHOD AND APPARATUS FOR THE PRECISE POSITIONING OF CELLS

[75] Inventor: Robert J. Klebe, Helotes, Tex.

[73] Assignee: Board of Regents, The University of Texas System, Austin, Tex.

[21] Appl. No.: 352,276

[22] Filed: Dec. 9, 1994

[51] Int. Cl.$^6$ .............................. C12Q 1/24; C12M 3/00
[52] U.S. Cl. ..................... 435/30; 435/1.1; 435/286.2; 435/286.4; 604/19; 604/290
[58] Field of Search ...................... 435/1.1, 30, 283.1, 435/286.2, 286.4; 364/413.08, 413.1; 604/19, 290

[56] References Cited

U.S. PATENT DOCUMENTS

| | | | |
|---|---|---|---|
| 4,656,130 | 4/1987 | Shoshan | 435/30 |
| 4,664,945 | 5/1987 | Maeda et al. | 427/96 |
| 4,791,069 | 12/1988 | Hovarka et al. | 436/533 |
| 4,874,500 | 10/1989 | Madou et al. | 204/412 |
| 4,877,745 | 10/1989 | Hayes et al. | 436/166 |
| 5,108,926 | 4/1992 | Klebe | 435/284 |

OTHER PUBLICATIONS

Klemperer, "Electron Optics," *UMI Books on Demand*, Second Edition, 1953.

Klebe et al., "Fibronectin–Mediated Attachment of Mammalian Cells to Polymeric Substrata," Chapter 38 of Proteins at Interfaces, ACS Symposium Series 343, eds. Brush and Horbett, pp. 615–628, 1987.

Klebe et al., "Adhesive Substrates for Fibronectin," *Journal of Cellular Physiology*, 109:481–488, 1981.

Klebe, "Cytoscribing: A Method for Micropositioning Cells and the Construction of Two–and Three–Dimensional Synthetic Tissues," *Experimental Cell Research*, 179:362–372, 1988.

*Primary Examiner*—David A. Redding
*Attorney, Agent, or Firm*—Arnold, White & Durkee

[57] ABSTRACT

Disclosed are a method and apparatus for the precise positioning of cells into highly organized tissue structures, which are suitable for use in the treatment of burn patients. Specific placement of cells onto substrata is obtained by the computer-controlled direct placement of cell suspension matrix material, which includes cells suspended by an extracellular matrix material, including cell adhesion proteins, collagens, gelatin (i.e., degraded collagen), and cyanoacrylates or other cellular glues. A fluorescence activated cell sorter is used to provide a stream or droplet stream of the biological material. Cells may also be positioned by means of computer-controlled placement of cell adhesion materials such as fibronectin to a substratum which is suitable for maintaining cell growth, followed by allowing cells to attach to those areas of the substratum where the cell adhesion material has been placed. These apparati may even be further modified and improved by providing a controlled biological environment in the area of the substratum, thus providing an integral unit for the production of organized tissues.

34 Claims, 3 Drawing Sheets

METHOD AND APPARATUS FOR THE PRECISE POSITIONING OF CELLS

The Government may have certain rights in the present invention pursuant to NIH grant CA33074.

BACKGROUND OF THE INVENTION

1. Field of the Invention

The present invention relates to methods and apparatus for the precise positioning of cells in a selected array or pattern on a separable substratum. More specifically, the invention relates to methods and apparatus for preparing tissues, and in particular, human tissues, having a precisely controlled cellular organization.

2. Description of the Related Art

The ability to prepare organized tissues or tissue-like structures starting with individual cells or colonies of cells is a science that is still in its infancy. However, tissue and even organ culture has progressed to a point such that it is now possible to routinely layer individual cells or colonies of most any particular cell type or types onto an appropriate solid matrix, and grow the layered cells in an appropriate medium until a randomly organized "tissue" is obtained. Although such tissues have a potentially wide range of usefulness, their primary utility has been in the field of tissue transplantation or replacement, for example, in plastic surgery and tissue reconstruction.

Tissue reconstruction employing tissues formed from cultured cells has found its most widespread application in the context of burn patient treatment. Traditionally, the treatment of burn victims has consisted primarily of debridement of the dead tissue, maintaining a sterile moist environment around the affected area, and allowing the body to produce scar tissue. While effective under optimal circumstances, such treatments suffer from potentially serious drawbacks due to the difficulty in maintaining the affected area in a sterile, moist environment. This inability can lead to serious repercussions such as severe infection, the leading cause of death in burn patients who survive the initial burn trauma.

More recently, attempts have been made to improve the treatment of burn patients through the use of a sterile layer of skin tissue that is grown in vitro and transplanted to cover the burned tissue. Such transplanted tissues serve the dual purpose of both protecting the affected area, by providing a physical barrier to infection, as well as aiding in maintaining the burned tissue in a humidified state. In such methods, cultures of freshly explanted dermis, preferably from the affected patient to be treated, are prepared by explanting dermal tissue, dissociating the tissue into individual cells, and culturing the dissociated cells in vitro to form a "tissue" layer. Once an integral tissue layer is obtained, it is transplanted to the burn patient to cover the affected area. While certain problems are addressed by this technique, including in particular, problems associated with tissue rejection, the method nevertheless has serious drawbacks. Most notable of these drawbacks is the inability to precisely structure and organize the cultured tissue in that many cell types are randomly positioned with respect to each other. Accordingly, the normal arrangement of cells in a normal tissue is generally not reproduced in the grafted tissue which can lead to a grafted tissue that is not normal in appearance, often colorless or blotched. In addition, cultured skin tissues currently in use lack sweat glands and, thus, such tissues lack physiologically important functions.

Accordingly, there is currently a need for novel approaches to the construction of transplantable tissues or tissue-like structure which would allow the precise positioning of cells into organized tissue structures for subsequent transplantation. Moreover, there is a need to provide techniques and apparatus which allow the orderly and reproducible formation of transplantable tissues into structures suitable for application to burn victims, for the production of synthetic veins or even organs, or other medical uses.

SUMMARY OF THE INVENTION

Accordingly, it is an object of the present invention to provide methods and apparatus which address at least some of these or other deficiencies in the art by allowing the precise positioning of cells to thereby form highly organized tissue structures.

It is an additional object of the invention to provide techniques suitable for the production of tissues for surgical application and, in particular, epidermal tissues for application in the treatment of burn patients.

It is a more particular object to provide techniques and apparatus for the cellular arrangement of tissues by the computer-controlled construction of two or three dimensional tissues of virtually any cell type and/or configuration.

Accordingly, the invention, in its most general and overall scope, is concerned with a method and apparatus for precisely locating cells on a separable substratum. As used herein, a "separable substratum" is defined as a solid matrix upon which cells may be grown. The matrix is separable in that it may be readily removed from underlying solid supports and freely transported. Moreover, in certain embodiments, the substratum is separable in that it is made of a material or treated in a manner such that, once cells have been positioned thereon and allowed to integrate into a tissue, the resultant tissue is separable from the substratum if so desired. In certain further embodiments, the substratum is simply a filter placed on absorbant material or a burn wound of a patient.

The invention thus embodies the realization that cells may be precisely positioned with respect to each other on a substratum, held in specific relative position by a cellular "glue" substance, and the cells allowed to grow together into a cohesive "tissue." Through the precise positioning of cellular glues (referred to herein as cell adhesion substances), through the precise positioning of the cells directly, or through the precise positioning of cells suspended in extracellular matrix material (referred to herein as cell suspension matrix material), cells are arranged with an accuracy of within that of a cell's diameter. The present invention contemplates the use of cell suspension matrix material provided by suspending cells in extracellular matrix materials, including but not limited to collagens and gelatin (i.e., degraded collagen). The extracellular matrix material acts as a "glue" that rapidly attaches cells to a substratum.

In certain embodiments, the invention is directed to an apparatus for positioning cells. The apparatus, in a general sense, embodies a solid support, a separable substratum layered on the solid support, a depositing means for depositing cell adhesion material, cells or cell suspension matrix material, and a translation means for positioning the separable substratum with respect to the depositing means to receive the cell adhesion material, cells, or cell suspension matrix material at selected points within an array.

The present invention contemplates a combination tissue culture device and an apparatus for the precise positioning of cell adhesion material on the tissue culture device for the cellular arrangement of tissue cultured thereon. The combination according to the present invention includes: a solid support, a substratum positioned on the solid support and constructed such that it is separable from the solid support and any tissue cultured thereon, a fluorescence activated cell sorter for emitting a stream or droplet stream of cell adhesion material through an orifice, and a computerized translation means for positioning the substratum with respect to the orifice to receive the stream or droplet stream of cell adhesion material at selected points within an array on the surface of the substratum.

The present invention further contemplates a combination tissue culture device and an apparatus for the precise positioning of cell suspension matrix material on the tissue culture device for the cellular arrangement of tissue cultured thereon. The combination according to the present invention includes: a solid support, a substratum positioned on the solid support and constructed such that it is separable from the solid support and any tissue cultured thereon, depositing means for emitting a stream or droplet stream of the cell suspension matrix material through an orifice, and a computerized translation means for positioning the substratum with respect to the orifice to receive the stream or droplet stream of the cell suspension matrix material at selected points within an array on the surface of the substratum. The present invention further contemplates the computerized translation means being a computer-controlled X-Y translation table coupled to the solid support, and the depositing means being a fluorescence activated cell sorter. In a further embodiment, the present invention contemplates using an Einzel lens to focus the droplet stream output from the fluorescence activated cell sorter.

The present invention further contemplates a method for precisely locating biological material on a separable substratum. The method includes the steps of positioning the substratum to receive from a fluorescence activated cell sorter a stream or droplet stream of the biological material through an orifice, and precisely positioning the separable substratum with respect to the orifice or the Einzel lens to receive the biological material from the fluorescence activated cell sorter at selected points within an array on the separable substratum utilizing a computerized translation means.

As used, herein, the phrase "selected points within an array" is meant to refer to points in an ordered geometric matrix, whether a two-dimensional or three-dimensional matrix. Accordingly, positioning at selected array points refers to any orderly reproducible placement which, for example, may be defined mathematically and stored in computer memory. Such positioning, therefore, generally cannot be obtained entirely by human hands, in that manual positioning is not sufficiently reproducible or rapid to allow the successful orderly layering of tissue components.

The cell adhesion materials of the present invention are molecules having an ability to bind to cell surfaces. Numerous such molecules are known in the art, from various classes of agents. For example, the most useful overall cell adhesion substance is fibronectin, a protein having a particular affinity for a specific cell-surface binding site on most cells. Accordingly, fibronectin, which is readily available to the art, serves as a useful cell gluing substance in the practice of the invention. However, it will be appreciated that the invention is in no way limited to fibronectin in that numerous useful adhesion substances are available to the art, including laminin, chondronectin, epinectin, epibolin, uromorulin and other cell adhesion proteins.

Moreover, in certain embodiments, it may be more convenient and/or advantageous to employ substances having a more particular affinity for specific cells and/or cell types. In such instances, it is desirable to use antibodies that specifically recognize an antigenic determinant on the surface of the desired cell type. In these instances, an appropriate amount of the antibody is positioned on the substratum and subsequently contacted with a cell suspension which includes the appropriate cell type to allow specific attachment of the cell type to the emplaced antibody.

The particular type or means of solid support is not crucial and may take any of a variety of forms or materials, so long as it serves to maintain the substratum in a suitably firm, relative placement during positioning of the cells or cellular adhesion material. It will often be the case that the support will be in the form of a platform contained within a biologically controlled environment. In this manner, an apparatus may be produced that embodies the invention in a self-contained structure, i.e., an apparatus which allows both the positioning of cells in one of various ways, as well as the culturing of the positioned cells sufficiently to form a transportable tissue. This support may also take the form of a patient's body to which cells are desired to be positioned.

Similarly, a depositing means is provided that is designed to deposit a stream or droplet stream of cell adhesion material, cells, or cell suspension matrix material. Typically, the depositing means will include a vessel that will contain an aliquot of cell adhesion material, cells, or cell suspension matrix material in a relatively isolated state, generally free of contamination such as debris or microbial growth. The vessel is typically connected to a housing through which the cell adhesion material, cells, or cell suspension matrix material is extruded to produce a stream or droplet stream. The housing includes at least one metered pore through which the material would flow out of the housing and onto the substratum. By "metered" it is meant that the flow of material through the pore is controlled, whether at the pore itself, as with an electrostatic or capillary attraction control in connection with a controlled rate of supply of the material from the vessel, or in connection with some means external to the housing. Depositing is preferably accomplished through the use of a fluorescence activated cell sorter, which provides a stream or droplet stream of biological material, in particular a droplet stream of cell suspension matrix material in which each droplet preferably includes a single cell.

The translating means is, in a general and functional sense, a structure which allows the specific positioning of the substratum to receive biological materials, such as cells, cell adhesion material, or cell suspension matrix material, from the depositing means in a desired pattern or array. Structures serving such a function may take a number of forms. For example, translating means may be accomplished through the use of computer-controlled translation tables that have movements which are reproducibly controllable and, preferably, rapid and precise.

A computer is typically employed to control the movement of the translation means. Through data processing techniques, a level of positioning control and speed is achieved such that an orderly and reproducible placement of material is realized in a period of time which is sufficiently short so as to render tissue construction in accordance herewith both economical and practical.

Useful substrata in accordance with the present invention are of four general types. In certain embodiments, substrata are employed to which cells will not attach, wherein the substrata has been treated with a coating of heat-inactivated protein such as albumin or virtually any other denatured protein. Such substrata are referred to herein as "negative-image" substrata because cells will not attach to the surfaces in the presence of heat inactivated protein, a negative image (i.e., no cell attachment) will be provided on the resultant surface. However, when these substrata are treated with cell adhesion material at selected points, they become adhesive to cells, even in the presence of heat-inactivated albumin, and thus become "positive-image" substrata at such positions which receive the adhesion material. Useful substrata that, in accordance with such embodiments, may variously serve as both positive or negative image surfaces, include numerous polymers, plastics, ceramics, metals or the like, including such materials as polystyrene, polymethylmethacrylate, polyvinylchloride, polyvinylacetate, Teflon®, cellulosics, pyrex glass, Carnauba wax, silicone, aluminum, culture plates, etc. Accordingly, depending on whether such materials are coated with heat inactivated protein, or alternatively one of the cell adhesion materials, the surface will be rendered either adhesive or nonadhesive to cell growth.

A second class of substrata are those to which cells will attach even following treatment with heat inactivated albumin. A preferred substrata of this class is collagen. Due to the specific interaction of the cell adhesion material with receptors on collagen, cells will attach to collagen in the presence of cell adhesion material even following treatment with heat inactivated albumin. Other substrata which will bind cell adhesion material and hence support cell growth even in the presence of albumin includes gelatin and synthetic collagen peptides.

A third class of useful substratum in accordance with the present invention include materials to which cells will not attach even in the presence of fibronectin, or one of the other cell adhesion materials, as well as in the presence of heat-inactivated albumin. Such surfaces include agar, and agar derivatives such as agarose or Sepharose®, polyhydroxyethyl methacrylate, to a certain extent polyacrylamide and, of course, bovine serum albumin itself.

A fourth class of useful substratum in accordance with the present invention include materials to which cell suspension matrix material will attach. Such materials include a Nucleopore filter, which may be pretreated with a small amount of newborn calf serum to greatly enhance wettability. An absorbant pre-filter may be placed below the filter to absorb excess fluid from the cell suspension matrix material. Such a pre-filter may be an absorbant glass fiber filter.

Accordingly, one will desire to choose one of the foregoing class of substrata depending on the particular circumstance. In this manner, the various surfaces, or surface treatments (e.g., coating with albumin), may be employed to obtain a selected placement of positive and negative "images," allowing the orderly arrangement of cells of differing types within the resultant tissue structure. For example, by specific placement of fibronectin at particular locations on a fibronectin-binding surface, followed by treatment of the surface with heat-inactivated albumin, cells will attach only to those positions containing fibronectin, thus providing a "positive" image at such points. Where collagen is used as a substratum, there is no need to pre-coat the surface with denatured protein in that cells will not directly attach to collagen. Thus, where collagen is employed as the substratum, negative areas may then be filled in by reapplication of cell adhesion materials followed by layering of a second cell type.

Surfaces of the third type (i.e., those that will not bind cells even in the presence of cell adhesion material) are useful in connection with cytoengraving embodiments of the present invention. In cytoengraving, a substratum such as agar is employed and a cell attachment surface such as those that will bind cells in the presence of fibronectin is applied to the non-attachment surface agar at locations where cell attachment is desired. In this manner, the agar surface is "stenciled" with a pattern to allow specific cell attachment to the pattern while leaving the background agar free of cell growth. Then, by removing the agar coating from various remaining positions, cell attachment may be achieved to such positions where the surface which underlies the agar is a cell attachment surface (i.e., a cell adhesion material-binding surface).

Further, the present invention presents a method for precisely locating cells on a substratum which includes the/steps of layering a separable substratum on a solid support, and stenciling the substratum by positioning cell suspension matrix material at selected points within an array on its surface. Stenciling the substratum will generally include precisely locating the substratum under a housing at computer specified array points over the surface of the substratum, the housing depositing a flow of cell suspension matrix material on the substratum, and having at least one metered pore through which the material may flow onto the substratum.

The advantages of the present invention will be further appreciated from the drawings and from the detailed description provided below.

BRIEF DESCRIPTION OF THE DRAWINGS

The herein described advantages and features of the present invention, as well as others which will become apparent, may be attained and understood in more detail by reference to the following description and appended drawings, which form a part of this specification.

It is to be noted, however, that the appended drawings illustrate only exemplary embodiments of the invention and are therefore not to be considered limiting of its scope, for the invention may admit to other equally effective embodiments.

DETAILED DESCRIPTION

The present invention relates to a technique, termed "cytoscribing," which is designed to enable one to establish precise spatial interrelationships between cells. In essence, cytoscribing involves the use of a computer for the high precision positioning of cells into predetermined patterns. Patterning devices commonly employed in the printing or computer graphics industry, such as an ink jet printer or graphics plotter, may be employed to position cells, either by positioning cell adhesion materials, or the cells themselves, onto a suitable substratum. In addition, a cytoengraving method, similar in approach to photoengraving techniques used in the silicon chip industry, may be utilized. This technique is employed to position cells to within a micron of a desired location. By utilizing and combining these devices and techniques, positive and negative patterns of cells (termed "cytoscripts") may be achieved, allowing the precise construction of two and three dimensional tissues.

These devices and techniques are thoroughly disclosed and described in detail in U.S. Pat. No. 5,108,926 to Klebe, which is hereby incorporated by reference in its entirety.

Although highly effective, these devices and techniques are limited in the use of cell adhesion proteins in micro-positioning cells by the overlapping specificity of cell adhesion proteins. The present invention provides an unexpected and surprisingly effective improvement to these devices and techniques that overcomes this limitation. In particular, the present invention provides for the micro-positioning of biological material utilizing a computer-controlled translation means for precise positioning of a substratum (e.g., computer-controlled X-Y translation table) and a depositing means for depositing a stream or droplet stream of biological material (e.g., a fluorescence activated cell sorter). Using this computer-controlled apparatus, it is possible to position large numbers of cells and establish precise spacial relationships between cells.

The apparatus and methods disclosed in U.S. Pat. No. 5,108,926 describe the positioning of cells by the deposition of cell adhesion proteins on a substratum. The micro-positioning of cells by the deposition of cell adhesion proteins on a substratum permits the precise positioning of cells because cells adhere where cell adhesion proteins have been deposited. The present invention, further allows the direct micro-positioning of cells by directing a stream or droplet stream of cell suspension matrix material onto a substratum which is positioned with the use of a computer-controlled translation means (e.g., computer-controlled X-Y translation table).

The present invention is more direct than prior systems and permits many new applications. While prior systems are limited to the micro-positioning of a few cell types on a single substrate due to the overlapping specificity of many cell adhesion proteins, the present system further permits the micro-positioning of an unlimited number of cell types onto a single substratum. The present invention allows one to deposit a first cell type on a substratum and then micro-position other cell types by repeating the process in an iterative manner. The novel process of the present invention avoids limitations that may have been imposed by the use of cell adhesion proteins in prior devices.

It is understood that the particular embodiment described below is simply one embodiment of the present invention. The biological material depositing means may be any device capable of delivering a reliable stream or droplet stream of biological material. The translation means may be any computer-controlled device that allows for precise and accurate micro-positioning (generally on the order of less than 20 µm positioning accuracy) of the separable substratum with respect to the stream or droplet stream of biological material. In particular, the depositing device will preferably provide a droplet stream of cell suspension matrix material, in which each droplet preferably includes a single cell. Although the present invention preferably contemplates the translation means positioning the substratum, it is understood that the translation means could position the delivery orifice of the depositing means, the substratum, or both.

Figure 1:
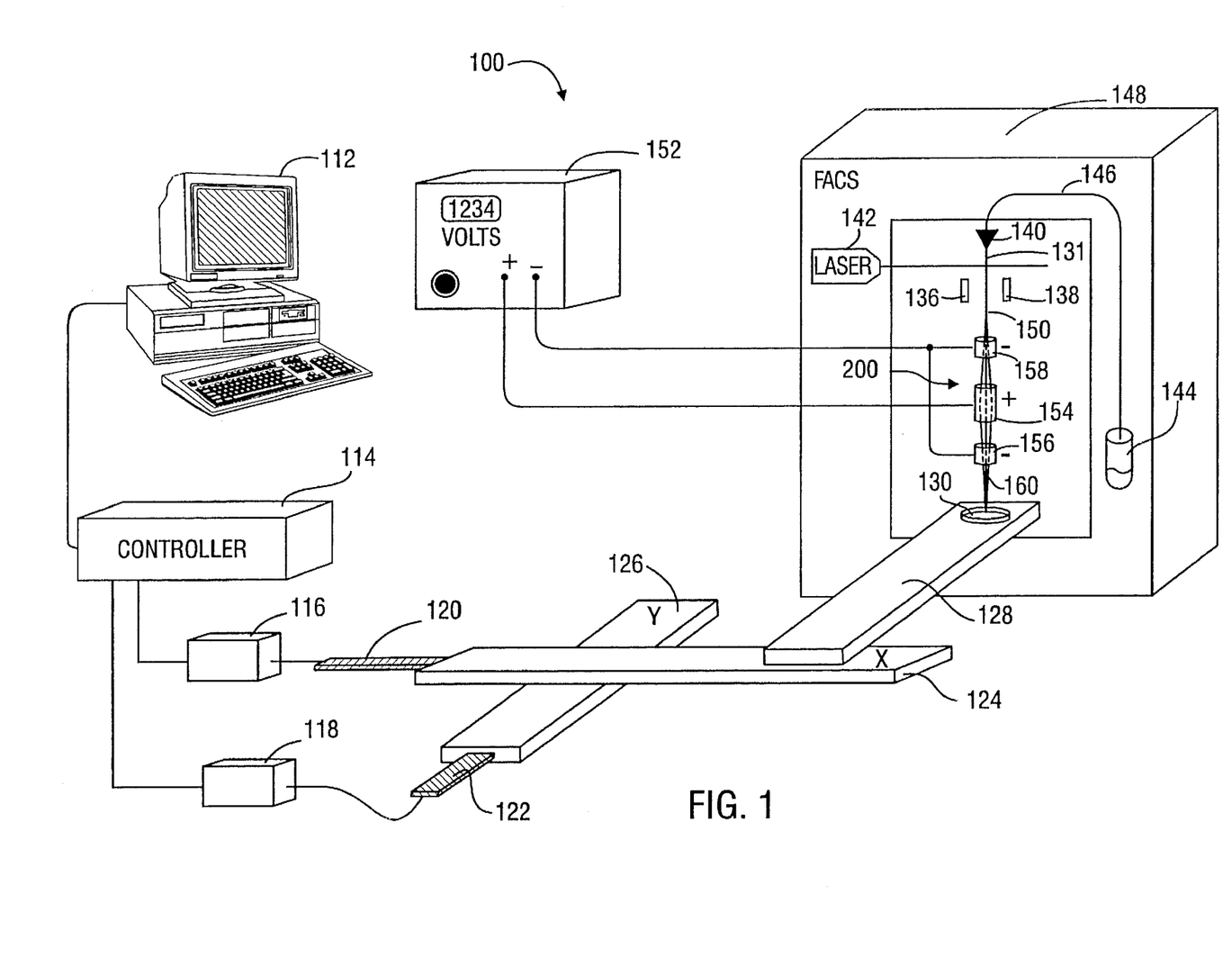
FIG. 1 is a diagram of an apparatus in accordance with the present invention.

FIG. 1 is a diagram of an apparatus according to the present invention. Apparatus 100 includes a depositing means in the form of a fluorescence activated cell sorter 148 ("FACS"). FACS 148 includes reservoir tube 144, which holds the biological material, connected through tube 146 to nozzle 140, which provides a cell delivery orifice. FACS 148 also includes laser analyzer 142 that may be use to analyze output stream 131 to determine the location of cells within the stream. Within FACS 148, stream 131 becomes a droplet stream and, using the information provided by laser analyzer 142, an electrical charge is placed on the droplets containing cells. Deflection plates 136 and 138, within FACS 148, may be used to deflect charged droplets into cell containing droplet stream 150. Non-charged droplets remain in a non-cell containing droplet stream (not shown). FACS are well known to those of skill in the art, and a FACS may be obtained from Becton Dickinson.

Separable substratum 130 is positioned to receive cell containing droplet stream 150 from FACS 148. Separable substratum 130 is coupled to translation tables 124 and 126. In particular, as shown in FIG. 1, separable substratum 130 may be connected to translation tables 124 and 126 by positioning board 128, which fits inside an opening in FACS 148, to allow droplet stream 150 to hit separable substratum 130. Apparatus 100 includes a translation means in the form of translation tables 124 and 126 that are computer-controlled. Computer controller 112 provides instructions to auxiliary controller 114, which relays instructions to translation table controllers 116 and 118, which in turn drive translation table stepper motors 120 and 122.

Further, a focussing system may be utilized to focus cell droplet stream 150 to obtain a more precise stream. For example, Einzel lens 200 may be used to focus cell droplet stream 150 provided by FACS 148. Power supply 152 (e.g., 0–10,000 volts) charges Einzel lens 200 to provide the necessary charge to produce the desired focussing effect. Droplet stream 150 will generally have some scattering due to the effect of droplet stream 150 leaving an orifice in nozzle 140. This scattering effect and the advantage of a focussing system is similar to that for electron optics in general. The principles of electron optics and focussing systems are well-known. See Klemperer, *Electron Optics*, pp. 1–15, 49–78 (2d ed. 1953).

Figure 2:
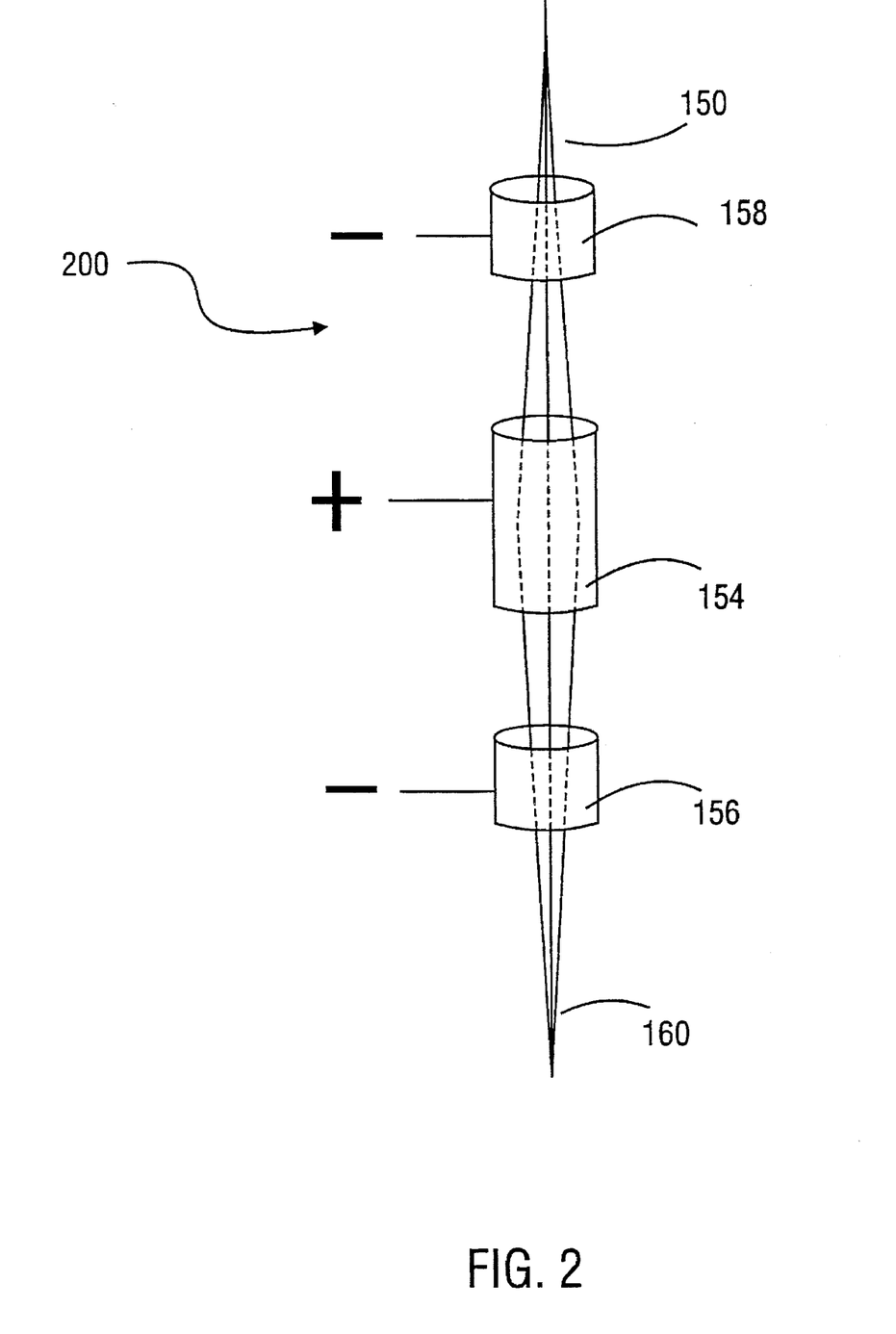
FIG. 2 is a diagram of a focussing system in accordance with the present invention.

FIG. 2 is a diagram of an Einzel lens according to the present invention. Einzel lens 200 may include copper cylinders 154, 156, and 158, which are charged by power supply 152. FIG. 2 is shown for the case where cell droplet stream 150 is charged positive. A positive charge is applied to copper cylinders 154, and copper cylinders 156 and 158 are grounded. The cooper cylinders 154, 156 and 158 act to focus the positively charged droplets in cell droplet stream 150 into focussed droplet stream 160. Use of an Einzel lens focusses stray droplets in the stream of cell-containing droplets and, thereby, increases the precision allowed by the present invention. An Einzel lens is a device which is commonly used in electronic applications to focus beams of charged particles (e.g., electron beams in television sets and subatomic particles in linear accelerators). The principles of the Einzel lens are well known, as discussed above.

FACS 148 may be a Becton Dickinson FACStar Plus. Nozzle 140 may be a 70 micron nozzle with Falcon #2052 tubes (5 ml). Translation tables 124 and 126 may be 106041P20M and 106101P20M translation tables. Computerized translation controllers 116 and 118 may be a S6DO translation table controllers. Stepper motors 120 and 122 may be S5783M0 stepper motors. Computer control may be provided by an AT6400 board placed in computer controller 112 and connected to an AT6400 auxiliary controller. Separable substrate 130 may be nucleopore membranes having 3 µm pore size (#28158-624) placed within a Falcon #1007 plastic petri plate.

FACS 148 may deposit biological material, such as cell suspension matrix material made from cells suspended in extracellular matrix materials, including but not limited to cell adhesion proteins, collagens, gelatin (i.e., degraded collagen), and cyanoacrylates or other cellular glues. The extracellular matrix material acts as a cell adhesion substance or "glue" that makes cells adhere to a surface upon contact. The stream of cell-containing droplets generated by FACS 148 remains stationary while separable substratum 130 is precisely positioned by computer-controlled translation tables 124 and 126 attached to positioning board 128. The biological material deposited by FACS 148 may also a simple cell suspension, including cells suspended in a saline solution.

In one possible use of the present invention, cell adhesion material may first be positioned at locations where attachment of a first cell type is desired. The positioning of the translation means is programmed to allow the rapid, reproducible deposition of material in whatever arrangement is required. Where a tissue is being formed for transplantation, one will generally desire to ensure that the distribution of each cell type employed in the final tissue is controlled and even. For example, where the first cell type employed in the construction include melanin-producing cells, one will desire to achieve an even distribution of deposited adhesion material, at a density determined by the desired resultant skin color tone. After the cell adhesion material is positioned, where the substratum used is one to which cells normally attach, the surface is treated with a denatured protein, such as denatured gelatin or albumin.

The denatured protein-treated substratum bearing the positioned cell adhesion material may then be contacted with a suspension of cells of the type which will be positioned first. After the cells have been allowed to attach to the adhesion-treated substratum, the suspension is drained and the surface washed. A second cell type may then be positioned by repositioning cell adhesion material to locations distinct from, and evenly distributed with respect to, the first positioned cell type. As before, the second cell type is positioned by contacting the substratum with a suspension of the second cell type.

These steps may be repeated until all of the various cell types have been positioned, except for the general epidermal cells. Prior to the addition of epidermal cells, or whatever cell type is employed for the general background of the "tissue", the entire remaining substratum is treated with cell adhesion material. Then a suspension of the final cell type is applied.

Where one employs different antibodies which recognize cell surface determinants of different cell types as the cell adhesion material, it will be appreciated that the number of steps will be reduced. In such cases, the various antibodies are positioned on the substratum at locations where attachment of the corresponding cell type is desired. Thus, for example, one will attach monoclonal antibodies which recognize melanin-producing cells at locations where melanin-producing cells are desired. Then, one would attach monoclonal antibodies at positions where the second cell type is desired, and so on. Finally, cell attachment is achieved by contacting the antibody-positioned substratum with a cell suspension which includes all of the desired cell types.

Further, where cell suspension matrix material is used, the positioning of the translation unit is programmed to allow the rapid, reproducible deposition of material in whatever arrangement is required. Because the cells in the cell suspension matrix material will be attached to the substratum by the extracellular matrix material, significant processing steps may be eliminated. The computer-controlled translation table may be first positioned at a "home" position. The first cell type is then sprayed onto the substratum in the programmed pattern. The computer-controlled translation table is then sent back to "home" and a second cell type is loaded. The second cell type is then sprayed on the substratum in the programmed pattern. Further cell types may be added using the same procedure. The use of cell suspension matrix material, therefore, allows for almost any cell line to be deposited by suspending the cells in an extracellular matrix material.

EXAMPLE

The substratum to be cytoscribed with FACS 148 was positioned by computer-controlled translation tables 124 and 126. The resolution of computer-controlled translation tables 124 and 126 exceeds dimensions of the cell to be cytoscribed. To easily observe cytoscribed cells, cells were deposited on a transparent polycarbonate filter. The resulting lines produced were approximately 500 µm wide, which amounted to about 20 cell diameters. Because the filter increased the time required for absorption of fluid into the pre-filter backing, some puddling of liquid occurred on the filter and, thus, the width of the lines formed on the filter was wider than could be achieved if cells were deposited directly on an absorbant material, such as a pre-filter or an absorbant collagen gel. The use of a FACS in cytoscription allows the preparation of tissue-like structures consisting of multiple cell types.

Cells may be positioned by moving the substratum with a computer-controlled X-Y translation table under a stream or droplet stream of cells produced by a FACS. The FACS serves the function of producing a stream of droplets, each of which preferably contains a single cell. The extracellular matrix material in which the cells are suspended acts as a glue to affix the suspended cells to a substratum. It is understood that in general any device may be used, instead of a FACS, that will produce a reliable stream or droplet stream of biological material.

In a particular application, an apparatus and method according to the present invention was used to cytoscribe the word "FACS" in a separable substratum. The motions required to cytoscribe the word "FACS" were programmed in G-code, the machine language for the computerized translation controller. An X-Y translation table was used for translation tables 124 and 126. A 56 cm long board was attached to the surface of the X-Y translation table to allow the insertion of a specimen under nozzle 140 of FACS 148.

The substrate material or separable substratum was then prepared. A 47 mm Nucleopore filter (3 µm pore size) was treated on both sides with a culture medium containing 0.01% newborn calf serum for about 30 seconds and then placed in a petri plate containing a 47 mm pre-filter that had been wetted with 2.1 ml of a culture medium containing either 0.01% newborn calf serum or neutral buffered formalin. Treatment of the filter with a small amount of serum greatly enhanced its wettability and resulted in a greatly enhanced ability of the filter to permit absorption of fluid into an absorbant pre-filter.

The cell suspension matrix material was provided by suspending Chinese Hamster Ovary ("CHO") (available from the American Type Culture Collection) cells at $10^6$ cells/ml in culture medium containing 0.6% gelatin (300 Bloom), available from Sigma Chemical Company. In addition, 1 ml of cell suspension matrix material was placed in a 5 ml plastic tube and attached to the input port of FACS 148. The settings for FACS 148 were then adjusted to select for cells, based on forward and right angle light scatter, at an output of 30 cells/second.

Figure 3:
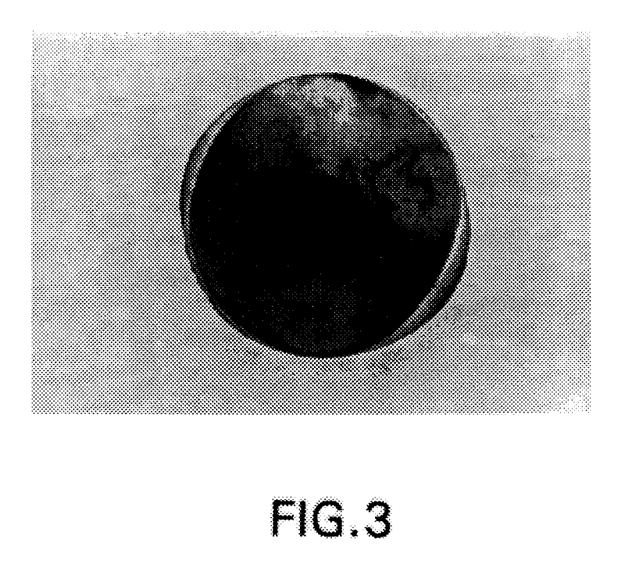
FIG. 3 is a photograph of a 47 mm Nucleopore polycarbonate filter cytoscribed with CHO cells using an apparatus and method according to the present invention.

The motion control program to cytoscribe "FACS" was then loaded into the memory of computer controller 112. The filter was place 16.5 cm from nozzle 140 of FACS 148 and the program was executed. Once motion had ceased, the filter was removed from FACS 148, separated from the neutral buffered formalin pre-filter, and air-dried. Alternatively, cells could be applied to a culture medium (0.01% serum) treated filter and cultured for at least 16 hours with comparable results. Cells attached to the filter were visualized by staining the filter with Toluidine Blue in 0.1M sodium acetate with pH 4.8. FIG. 3 shows the resulting filter with the word "FACS" cytoscribed.

This example demonstrates a novel and highly advantageous computer directed technique that permits one to position a wide variety of cells with high precision in virtually any desired pattern. The methods described take advantage of (a) the capabilities of computer-controlled translation units, and (b) the adhesion nature of the extracellular matrix material of cell suspension matrix material.

With the aid of the methods described herein, three-dimensional tissues can be constructed by staking two-dimensional tissues in layers. Thus, cytoscribing provides a facile means of establishing precise spatial arrangements within large populations of cells and, thereby, permits new approaches to be made towards the preparation of highly organized tissue-like structures for application to burn victims.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size, and arrangement of parts. For example, equivalent elements or materials may be substituted for those illustrated and described herein, and certain features of the invention may be utilized independently of the use of other features, all as would be apparent to one skilled in the art after having the benefit of this description of the invention.

What is claimed is:

1. A combination tissue culture device and an apparatus for the precise positioning of cells on the tissue culture device for the cellular arrangement of tissue cultured cells thereon, the combination comprising:

a solid support;

a substratum positioned on said solid support and constructed such that it is separable from said solid support and any tissue cultured thereon;

a fluorescence activated cell sorter positioned to deposit a stream or droplet stream of cell suspension matrix material on said substratum;

an Einzel lens positioned to focus said stream or droplet stream of cell suspension matrix material into a focused stream or droplet stream; and a computer-controlled X-Y translation table coupled to said solid support to provide precise positioning of said solid support relative to said focused stream or droplet stream of cell suspension matrix material.

2. A combination tissue culture device and an apparatus for the precise positioning of cells on the tissue culture device for the cellular arrangement of tissue cultured cells thereon, the combination comprising:

a solid support;

a substratum positioned on said solid support and constructed such that it is separable from said solid support and any tissue cultured thereon;

depositing means for emitting a stream or droplet stream of cell suspension matrix material through an orifice, said depositing means being a fluorescence activated cell sorter; and a computerized translation means for positioning said substratum with respect to said orifice to receive said stream or droplet stream of said cell suspension matrix material at selected points within an array on the surface of said substratum.

3. The apparatus of claim 2, further comprising:

a focusing system coupled to said fluorescence activated cell sorter to focus said cell suspension matrix material emitted through said orifice of said fluorescence activated cell sorter.

4. The apparatus of claim 3 wherein said focusing system is an Einzel lens.

5. A method for precisely locating biological material on a separable substratum comprising:

positioning said separable substratum to receive from a fluorescence activated cell sorter a stream or droplet stream of biological material through an orifice;

emitting a stream or droplet stream of said biological material from said fluorescence activated cell sorter; and precisely positioning said separable substratum with respect to said orifice to receive said emitted stream or droplet stream of biological material from said fluorescence activated cell sorter at selected points within an array on said separable substratum utilizing a computerized translation means.

6. The method of claim 5, wherein said biological material is cell adhesion material.

7. The method of claim 5, wherein said biological material is cell suspension matrix material.

8. The method of claim 7, further comprising focusing said emitted stream or droplet stream of cell suspension matrix material with an Einzel lens, before said precisely positioning step.

9. The method of claim 7, wherein said separable substratum is a burn wound of a patient.

10. A combination tissue culture device and an apparatus for the precise positioning of cells or cell adhesion material on the tissue culture device for the cellular arrangement of tissue cultured cells thereon, the combination comprising:

a solid support;

a substratum positioned on said solid support and constructed such that it is separable from said solid support and any tissue cultured thereon;

a fluorescence activated cell sorter for emitting a stream or droplet stream of cells or cell adhesion material through an orifice; and a computerized translation means for positioning said substratum with respect to said orifice to receive said stream or droplet stream of cells or cell adhesion material at selected points within an array on the surface of the substratum.

11. The combination of claim 10 wherein said cell adhesion material is selected from the group consisting of fibronectin, laminin, chondronectin, epinectin, epibolin and uromorulin.

12. The combination of claim 10 wherein the cell adhesion material comprises an antibody having specificity for a cell surface determinant.

13. The combination of claim 10 wherein said substratum is selected from the group consisting of collagen, polylactide, pyrex glass, Carnauba wax, silicone, aluminum, polytetrafluoroethylene, polyvinylacetate, polyvinylchloride and polystyrene.

14. The combination of claim 10 wherein said substratum comprises collagen in the form of a wafer or sheet.

15. The combination of claim 10 wherein said cells are cells suspended in a saline solution.

16. The combination of claim 10 wherein said computerized translation means comprises a computer-controlled X-Y translation table coupled to said solid support.

17. A combination tissue culture device and an apparatus for the precise positioning of cells on the tissue culture device for the cellular arrangement of tissue cultured cells thereon, the combination comprising:

a solid support;

a substratum positioned on said solid support and constructed such that it is separable from said solid support and any tissue cultured thereon;

depositing means for generating a stream or droplet stream of biological material, said depositing means being capable of determining cell containing droplets, if present, within a droplet stream of biological material and being capable of sorting said cell containing droplets from non-cell containing droplets to form a cell containing stream or droplet stream of biological material; and a computerized translation means for positioning said substratum with respect to said stream or droplet stream of biological material so that said substratum receives said stream or droplet stream of biological material at selected points within an array on the surface of said substratum.

18. The combination of claim 17 further comprising means for biologically controlling the environment surrounding the substratum.

19. The combination of claim 17 wherein said substratum is a filter placed on an absorbent pre-filter.

20. The combination of claim 17 wherein said computerized translation means comprises a computer-controlled X-Y translation table coupled to said solid support.

21. The combination of claim 20 wherein said computerized translation means is movable to selected points with a two-dimensional array.

22. The combination of claim 20 wherein said computerized translation means is movable to selected points within a three-dimensional array.

23. The combination of claim 17 wherein said depositing means also includes a container holding a quantity of biological material, said biological material being cell suspension matrix material.

24. The combination of claim 23 wherein said cell suspension matrix material comprises collagen.

25. The combination of claim 17, wherein said cell containing stream or droplet stream comprises a plurality of droplets with substantially all of said plurality of droplets containing at least one cell.

26. The combination of claim 25, wherein substantially all cell containing droplets contain only a single cell.

27. The combination of claim 17, wherein said depositing means is a fluorescence activated cell sorter.

28. The combination of claim 17, wherein said computerized translation means moves said solid support while said depositing means remains stationary.

29. The combination of claim 17, wherein said computerized translation means moves said depositing means while said solid support remains stationary.

30. The combination of claim 17, wherein said depositing means includes charged plates for deflecting said cell containing droplets to form said cell containing stream or droplet stream.

31. A method for precisely locating biological material on a separable substratum comprising:

positioning said separable substratum to receive a stream or droplet stream of biological material;

generating a droplet stream of biological material;

determining cell containing droplets within said droplet streams, if present;

sorting said cell containing droplets, if present, from non-cell containing droplets to form a cell containing stream or droplet stream of biological material; and positioning said separable substratum and said stream or droplet stream of biological material with respect to each other so that said separable substratum receives said stream or droplet stream of biological material at selected points within an array on said separable substratum utilizing a computerized translation means.

32. The method of claim 31, wherein said biological material is cell adhesion material.

33. The method of claim 31, wherein said biological material is cell suspension matrix material.

34. The method of claim 33, wherein said separable substratum is a burn wound of a patient.

* * * * *